(12) United States Patent
Marchitto et al.

(10) Patent No.: US 7,647,099 B2
(45) Date of Patent: Jan. 12, 2010

(54) CONTROLLED RELEASE TRANSDERMAL DRUG DELIVERY

(75) Inventors: Kevin S. Marchitto, Golden, CO (US); Stephen T. Flock, Arvada, CO (US)

(73) Assignee: Rocky Mountain Biosystems, Inc., Golden, CO (US)

( * ) Notice: Subject to any disclaimer, the term of this patent is extended or adjusted under 35 U.S.C. 154(b) by 887 days.

(21) Appl. No.: 10/422,288

(22) Filed: Apr. 24, 2003

(65) Prior Publication Data

US 2003/0204163 A1   Oct. 30, 2003

Related U.S. Application Data

(60) Provisional application No. 60/376,112, filed on Apr. 29, 2002.

(51) Int. Cl.
*A61N 1/30*   (2006.01)

(52) U.S. Cl. .................................................. 604/20

(58) Field of Classification Search .............. 604/20, 604/65–66, 290, 890.1, 19, 21, 22, 27–28, 604/46, 48, 289, 501; 600/309, 310, 316, 600/345, 365, 372–373, 377, 378, 381, 573, 600/583, 391; 606/9, 32, 41, 42, 43, 44, 606/45, 48, 131, 27, 28, 159; 607/2, 96, 607/98, 99, 3, 100, 103, 104, 108
See application file for complete search history.

(56) References Cited

U.S. PATENT DOCUMENTS

| 5,084,006 | A | * | 1/1992 | Lew et al. | 604/20 |
| 5,496,266 | A | * | 3/1996 | Haak et al. | 604/20 |
| 5,533,971 | A | * | 7/1996 | Phipps | 604/20 |

* cited by examiner

*Primary Examiner*—Manuel A Mendez
(74) *Attorney, Agent, or Firm*—Benjamin Aaron Adler

(57) ABSTRACT

Provided herein is a device for controlling the release of a substance at a site of interest in a biological membrane comprising a means of monitoring a physiological state at the site of interest; and a means of releasing a variable amount of the substance to the site of interest where the amount varies in response to the status of the monitored physiological state. Also provided are methods of using the device.

23 Claims, 1 Drawing Sheet

CONTROLLED RELEASE TRANSDERMAL DRUG DELIVERY

CROSS-REFERENCE TO RELATED APPLICATION

This non-provisional patent application claims benefit of provisional patent applications No. 60/376,112, filed Apr. 29, 2002, now abandoned.

BACKGROUND OF THE INVENTION

1. Field of the Invention

The present invention relates generally to the fields of biomedical physics and drug delivery. More specifically, the present invention provides a device and methods for controlling the release of a substance across biological membranes and for controlling subsequent results between treatment sites.

2. Description of the Related Art

Various methods have been used for facilitating the delivery of compounds across the skin and other membranes. Iontophoresis uses an electric current to increase the permeation rate of charged molecules. However, iontophoresis is dependent on charge density of the molecule and, furthermore, has been known to cause burning in patients. Use of ultrasound also has been tested whereby application of ultrasonic energy to the skin results in a transient alteration of the skin which leads to an increased permeability to substances. Electromagnetic energy produced by lasers may be used to ablate the stratum corneum in order to make the skin more permeable to pharmaceutical substances (U.S. Pat. No. 4,775, 361). Impulse transients generated by lasers or by mechanical means may be used to make alterations in epithelial layers that result in improved permeation of compounds (U.S. Pat. No. 5,614,502).

In general permeation of drugs through the skin occurs at a very slow rate, if at all. The primary rate-limiting step in this process is the passage of these compounds through the outermost layer of skin, i.e., the stratum corneum. The stratum corneum is a very thin layer of dead cells that acts as an impermeable layer to matter on either side of this layer and primarily provides the skin's barrier function. It has long been recognized that loss or alteration of the stratum corneum results in increased permeability to many substances; materials can diffuse more easily into or out of the skin. It also has been demonstrated that electromagnetic energy induced alterations of the stratum corneum result in increased permeability to substances as disclosed in U.S. Pat. Nos. 6,315,722, 6,251,100, 6,056,738 and 5,643,252. Alternatively, compounds referred to as permeation enhancers, e.g., alcohol or drug carriers such as liposomes, can be used, with some success, to penetrate the stratum corneum. The barrier function of the skin presents a very significant problem to pharmaceutical manufacturers interested in topical administration of drugs or in cutaneous collection of bodily fluids.

Electrosurgery is a method whereby tissue coagulation and/or dissection can be effected. In electrosurgery radiofrequency (RF) current is applied to tissue by an active electrode. In a bipolar system the current is passed through tissue between two electrodes on the same surgical instrument, such as a forceps. In a monopolar system a return-path (ground) electrode is affixed in intimate electrical contact with some part of the patient. Because of the importance of the ground electrode providing the lowest impedance conductive path for the electrical current, protection circuits monitoring the contact of the ground with the patient are often employed wherein an increase in ground electrode-skin impedance results in the instrument shutting down. A desired alteration in the tissue, which usually is coagulation or cutting, can be made by manipulating the treatment electrode shape, the electrode position (contact or non-contact) with respect to the tissue surface, frequency and modulation of the radiofrequency current, power of the radiofrequency current and the length of time it is applied to the tissue surface, and peak-to-peak voltage of the radiofrequency current with respect to the tissue type.

For example, decreasing electrode size translates into increased current density in the tissue proximal to the electrode and so a more invasive tissue effect, such as dissection as compared to coagulation, is realized. Similarly, if the electrode is held close to the tissue but not in contact, then the area of radiofrequency-tissue interaction is smaller as compared to the area when the electrode is in contact with the tissue, therefore, the effect on the tissue is more invasive. By changing the waveform of the applied radiofrequency current from a continuous sinusoid to packets of higher peak voltage sinusoids separated by dead time (i.e. a duty cycle of 6%), then the tissue effect can be changed from dissection to coagulation. Increasing the voltage of the waveform increases the invasiveness of the tissue effect and the longer the tissue is exposed to the radiofrequency, the greater the tissue effect. Finally, different tissues respond to radiofrequency differently because of their different electrical conductive properties, concentration of current-carrying ions, and different thermal properties. In a typical electrosurgical system, radiofrequency frequencies of 300 kHz to 4 MHz are used as nerve and muscle stimulation cease at frequencies beyond 100 kHz.

Devices incorporating radio frequency electrodes for use in electrosurgical and electrocautery techniques are described in Rand[1] et al. and U.S. Pat. Nos. 5,281,216, 4,943,290, 4,936, 301, 4,593,691, 4,228,800, and 4,202,337.

U.S. Pat. Nos. 4,943,290 and 4,036,301 describe methods for injecting non-conducting liquid over the tip of a monopolar electrosurgical electrode to electrically isolate the electrode, while energized, from a surrounding electrically conducting irrigant.

U.S. Pat. Nos. 5,195,959 and 4,674,499 describe monopolar and bipolar electrosurgical devices that include a conduit for irrigating the surgical site.

U.S. Pat. Nos. 5,217,455, 5,423,803, 5,102,410, 5,282, 797, 5,290,273, 5,304,170, 5,312,395, 5,336,217 describe laser treatment methods for removing abnormal skin cells, such as pigmentations, lesions, soft tissue and the like.

U.S. Pat. Nos. 5,445,634 and 5,370,642 describe methods for using laser energy to divide, incise or resect tissue during cosmetic surgery. U.S. Pat. No. 5,261,410 is directed to a method and apparatus for detecting and removing malignant tumor tissue.

U.S. Pat. Nos. 5,380,316, 4,658,817, 5,389,096, International Publication WO 94/14383 and European Patent Application No. 0515867 describe methods and apparatus for percutaneous myocardial revascularization. These methods and apparatus involve directing laser energy against the heart tissue to form transverse channels through the myocardium to increase blood flow from the ventricular cavity to the myocardium.

Devices and methods disclosed in U.S. Pat. Nos. 5,683, 366, 5,697,536, 6,228,078, and 5,888,198 are bipolar and monopolar RF electrosurgical devices that use a method of tissue disintegration as a means to ablate tissue prior to myocardial revascularization, tissue resurfacing or other surgical procedures.

Devices and methods for drug delivery using laser ablation systems have been described. U.S. Pat. No. 6,251,100 provides an improved method of administering a pharmaceutical composition, such as an anesthetic through the skin of a patient without the use of a sharp or needle. This method includes the step of irradiating the stratum corneum of a region of the skin of the patient using a laser. By a selection of parameters, the laser irradiates the surface of the skin precisely to a selectable depth without causing clinically relevant damage to healthy proximal tissue. A pharmaceutical composition is then applied to the region of irradiation. International Publication WO 00/57951 describes the use of non-ionizing energy, including lasers, to improve methods of administering pharmaceuticals in tissues, including the skin. In the case of RF energy certain applications describe feedback mechanisms that are used to prevent damage to viable tissue in the area surrounding the treatment site including U.S. Patent Publication No. 2002/0010414 A1 and WO 01/21068.

It is notable that consistent means of treatment are desirable. The Code of Federal Regulations (21 CFR 860.7(e)(1)) establishes that there is "reasonable assurance that a device is effective when it can be determined, based upon valid scientific evidence, that in a significant portion of the target population, the use of the device . . . will provide clinically significant results." Devices that cannot be shown to provide consistent results between patients, or even within a patient upon multiple use, will have minimal utility and may not be approvable for broad use.

Beyond devices it is generally desirable to develop medical products with critical controls that can deliver a precise result. Of critical concern is the delivery of many types of drugs. Certain drugs can be described as having a "broad" or "narrow" therapeutic index (TI). That is, some drugs may be useful over a broad range of concentrations (broad TI), and thus are safe for the general population, while other drugs may only be effective over a narrow concentration range (narrow TI) and may even be dangerous when administered in greater than recommended concentrations. This is particularly true where a drug has a narrow therapeutic index; the delivery of the drug must be controlled carefully so as to avoid potentially harmful effects.

The FDA in its PMA Memorandum #P91-1: Clinical Utility and Premarket Approval has established that devices that cannot be controlled may have limited utility. Particularly a drug delivery device may have limited utility if no assurance can be made that a consistent dosage is delivered throughout the patient population.

The drug-device combination must be capable of consistently delivering a dosage. As part of INDs and NDAs for administered drug products, bioavailability studies focus on determining the process by which a drug is released from the oral dosage form and moves to the site of action. Bioavailability data provide an estimate of the fraction of the drug absorbed, as well as the drug's subsequent distribution and elimination. Bioavailability is defined in 21 CFR 320.1 as "the rate and extent to which the active ingredient or active moiety is absorbed from a drug product and becomes available at the site of action. For drug products that are not intended to be absorbed into the bloodstream, bioavailability may be assessed by measurements intended to reflect the rate and extent to which the active ingredient or active moiety becomes available at the site of action." This definition focuses on the processes by which the active ingredients or moieties are released from a dosage form and move to the site of action. A delivery device which does not consistently release the same levels of a drug product due to the design of a product will have limited clinical utility as there can be no assurance that a certain dosage has been delivered at any point in time.

Furthermore, studies to establish bioequivalence between two products are important to demonstrated safety and therapeutic efficacy in a product and will be a benchmark for approval of drugs by regulatory bodies. Bioequivalence is defined in 21 CFR 320.1 as "the absence of a significant difference in the rate and extent to which the active ingredient or active moiety in pharmaceutical equivalents or pharmaceutical alternatives becomes available at the site of drug action when administered at the same molar dose under similar conditions in an appropriately designed study." As noted in the statutory definitions, both bioequivalence and product quality bioavailability focus on the release of a drug substance from a drug product and subsequent absorption into the systemic circulation. Where the test product generates variable effect at the site of action, as compared to those of the reference product, the product cannot be claimed as consistent, will not have great clinical utility and could be dangerous to use.

Control of delivery for transdermal applications is achieved by delivering a fraction of what is "absorbable," and either regulating the size of the dosage or the amount that is released from the vehicle. The condition of the skin and its hydration are significant factors in the percutaneous absorption of drugs. Some solubility of the substance in both lipid and water is thought to be essential. The aqueous solubility of a drug determines the concentration presented to the absorption site and the partition coefficient strongly influences the rate of absorption across the absorption site (Pharmaceutical Dosage Forms and Drug Delivery Systems, Ansel, H. C., Popovich, N. G. Allen, L. V. Eds., Williams & Wilkins, Baltimore, 1995). Vehicles that increase the hydration of the skin generally favor percutaneous absorption of drugs.

Consistency in the delivery of the substance to the target site may also be achieved through modulation of the device itself, such that variable amounts of the substance are released based on the condition of the target site. Factors such as hydration, electrochemical state, and conductivity may all be used as a means to assess the condition of the target site, and the substance may be released in response to those conditions. Control over iontophoretic drug delivery devices based on impedence are described U.S. Pat. Nos. 6,167,301 and 6,208,891.

The inventors have recognized a need in the art for a device and improved methods of controllably moving substances across biological membranes in a manner that yields subsequent corresponding results within an individual or within a group of individuals. Specifically, the use of electromagnetic energy to alter the permeability of a biological membrane to a pharmaceutical or other biological molecule has been reported, however, the prior art is deficient in reports of methods for controlling the delivery or collection of a substance in response to a specific physiological state of the biological membrane. The present invention fulfills this longstanding need and desire in the art.

SUMMARY OF THE INVENTION

In one embodiment of the present invention there is provided a device for controlling the release of a substance at a site of interest in a biological membrane comprising a means of monitoring a physiological state at the site of interest; and a means of releasing a variable amount of the substance to the site of interest; said amount varying in response to the status of the monitored physiological state.

In another embodiment of the present invention there is provided a method to control the release of a substance at a site of interest in a biological membrane using the device disclosed supra by contacting the site of interest with the device; monitoring a physiological state at the site of interest; applying an algorithm to evaluate the physiological state; operating a release mechanism in the device in response to the value obtained for the physiological state; and releasing the substance to the site of interest or collecting the substance from the site of interest thereby controlling the release of the substance at the site of interest.

In yet another embodiment of the present invention there is provided a device for controlling the release of a substance at a site of interest on a biological membrane comprising a means for ablating or altering the biological membrane at the site of interest; a means of monitoring a physiological state at the site of interest; a means of releasing a variable amount of the substance to the site of interest; the amount varying in response to the status of the monitored physiological state; and a means for housing the device.

In still another embodiment of the present invention there is provided a method to control the release of a substance at a site of interest in a biological membrane comprising the steps of contacting the site of interest with the device disclosed supra; ablating or altering the biological membrane at the site of interest; monitoring a physiological state at the site of interest; applying an algorithm to evaluate the physiological state; operating a release mechanism in the device in response to the value obtained for the physiological state; and releasing the substance to the site of interest or collecting the substance from the site of interest thereby controlling the release of the substance at the site of interest.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
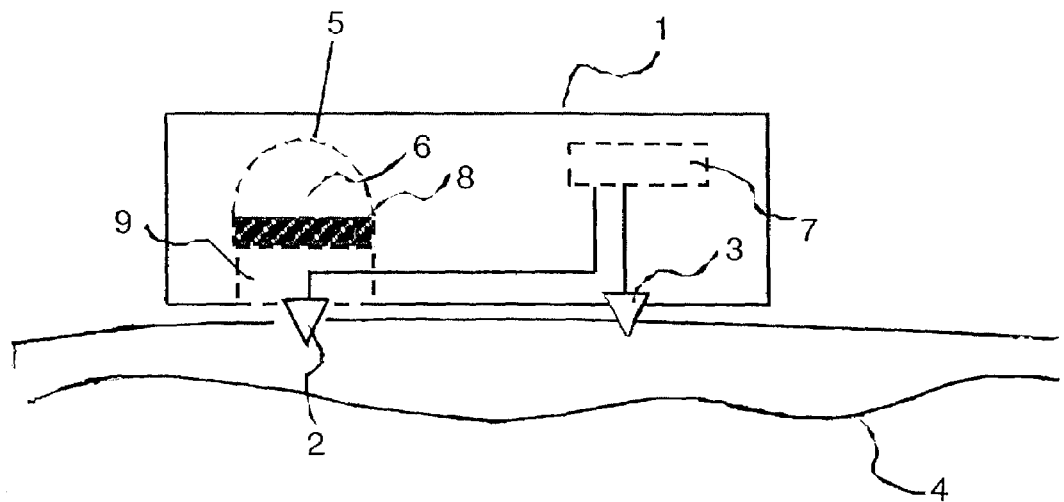
FIG. 1 shows a schematic of a device used for controlling the release of a substance to a site.

In one embodiment of the present invention there is provided a device for controlling the release of a substance at a site of interest in a biological membrane comprising a means of monitoring a physiological state at the site of interest; and a means of releasing a variable amount of the substance to the site of interest; said amount varying in response to the status of the monitored physiological state.

In an aspect of this embodiment the means to monitor the physiological state may be at least one first active electrode, which is an anode, in electrical contact at the site of interest; a second return electrode, which is a cathode, in electrical contact distal to the first electrode at the site of interest; and a controller to monitor an electrical current between the first electrode and second electrode, where the controller includes a microprocessor.

Further in this aspect the means of releasing the variable amount of the substance comprises a reservoir to contain the substance; and a release mechanism located between the reservoir and the site of interest; the mechanism operably connected to a controller; wherein operation of the mechanism by the controller releases the substance from the reservoir to the site of interest or collects the substance in the reservoir from the site of interest. Optionally, the releasing means may have a permeable membrane located between the release mechanism and the site of interest, where the permeable membrane is in contact with the site of interest or in contact with a fluid at the site of interest. The release mechanism may be a valve, a membrane or an electronic pump device. An example of an electronic pump device is an electrophoretic device.

In another aspect of this embodiment the means of monitoring the physiological state may be at least one probe which further has an electrical sensor, a chemical sensor or a mechanical sensor located at the tip of the probe(s) where the sensor is in contact with the site of interest; and a controller to monitor the probe(s), where the controller further includes a microprocessor.

In all aspects of this embodiment the device may be in a patch. The biological membrane may be the skin which further may be altered or ablated at the site of interest. The physiological states monitored may be an electrical property or a chemical property at the site monitored. Representative examples of electrical properties are impedance, conductivity or resistance. Representative examples of a chemical property include hydration, one or more ion levels at the site or the level of lipids, proteins or carbohydrates at the site of interest.

The substances used in this and other embodiments may be a diagnostic material or biological molecules such as pharmaceutical compounds. Representative examples of such compounds are nitroglycerin, an anti-nauseant, a hormone, a steroidal antiinflammatory agent, a non-steroid anti-inflammatory agent, a chemotherapeutic agent, an anti-cancer agent, an immunogen, an anti-viral agent or an anti-fungal agent. A representative example of an anti-nauseant is scopolamine. Representative examples of an antibiotic are tetracycline, streptomycin, sulfa drugs, kanamycin, neomycin, penicillin, or chloramphenicol. Representative examples of a hormone is LHRH, parathyroid hormone, growth hormone, gonadotropins, insulin, ACTH, somatostatin, prolactin, placental lactogen, melanocyte stimulating hormone, thyrotropin, parathyroid hormone, calcitonin, enkephalin, or angiotensin.

In another embodiment of the present invention there is provided a method to control the release of a substance at a site of interest in a biological membrane using the device disclosed supra by contacting the site of interest with the device; monitoring a physiological state at the site of interest; applying an algorithm to evaluate the physiological state; operating a release mechanism in the device in response to the value obtained for the physiological state; and releasing the substance to the site of interest or collecting the substance from the site of interest thereby controlling the release of the substance at the site of interest.

In an aspect of this embodiment the value obtained for the physiological state is a control value that is compared to subsequently obtained values for the physiological state. These subsequently obtained values of the physiological state may be obtained from the same individual or from within a group of individuals. All other aspects of this embodiment such as the device, the biological membrane, the physiological states monitored and substances are as disclosed supra.

In yet another embodiment of the present invention there is provided a device for controlling the release of a substance at a site of interest on a biological membrane comprising a means for ablating or altering the biological membrane at the site of interest; a means of monitoring a physiological state at the site of interest; a means of releasing a variable amount of the substance to the site of interest; the amount varying in response to the status of the monitored physiological state; and a means for housing the device.

In this embodiment the ablating or altering means is an energy delivery system which delivers laser energy, electromagnetic energy, mechanical energy, heat energy, or energy in the form of ions, neutral particles or a plasma. The means of monitoring the physiological state are at least as disclosed supra. Optionally, the monitoring means may use an electrically conductive fluid interface between the electrodes disclosed and the biological membrane. Additionally, the first and second electrodes as disclosed may form part of a galvanic cell.

Also in this embodiment the means of releasing the variable amount of said substance is a patch which comprises a reservoir to contain said substance; and a release mechanism. The reservoir and release mechanism are as disclosed supra. Furthermore, all other aspects of this embodiment such as aspects of the device, the biological membrane, the physiological states monitored and substances are as disclosed supra.

In still another embodiment of the present invention there is provided a method to control the release of a substance at a site of interest in a biological membrane comprising the steps of contacting the site of interest with the device disclosed supra; ablating or altering the biological membrane at the site of interest; monitoring a physiological state at the site of interest; applying an algorithm to evaluate the physiological state; operating a release mechanism in the device in response to the value obtained for the physiological state; and releasing the substance to the site of interest or collecting the substance from the site of interest thereby controlling the release of the substance at the site of interest. Again, all other aspects of this embodiment such as aspects of the method, aspects of the device, the biological membrane, the physiological states monitored and substances are as disclosed supra.

The present invention provides devices and methods for improving the permeability of the skin or other biological membranes to certain substances and a means for controlling the amount of the substance released to the site. Alternatively, the device may be used to collect substances from the treatment site. Targets associated with tissue interfaces are made permeable to diagnostic and therapeutic substances. The device and methods disclosed herein can improve the permeation rate of pharmaceuticals across a biological membrane into an individual or can increase the diffusion of substances out of a tissue of the individual.

The system allows the operator to cause molecular alterations in necrotic tissue or dead cells present in, for example, the stratum corneum by selectively applying energy, e.g., electromagnetic energy, laser energy, mechanical energy, heat energy, or energy in the form of ions, neutral particles or a plasma, to the skin prior to the application of a desired substance. The transient or sustained molecular alteration of membranes and tissue interfaces induced by this energy or by the physical products of the interaction of the energy improve permeability to the particular substance, but also result in electrical, chemical and hydration changes to the membrane such that these changes can be measured as an indication of the relative permeability of the membrane. This information on relative permeability may be used by the device to adjust the amount of the substance released. The system is useful for the delivery of substances, for example, delivery of drugs and diagnostic agents or for the collection of biomolecules, for example, insulin.

The devices described herein can be used to measure the integrity of the stratum corneum in order to determine the potential for permeability to substances, including drugs and other medically useful compounds. As successive layers of the stratum corneum are removed, percutaneous permeation generally increases until a maximum rate of permeation or flux occurs at which point the stratum corneum is completely removed. Thus, by measuring the depth or degree of reduction, one may use the information to control the flux of a desired substance.

The present devices alter the stratum corneum in a manner that exposes increasingly hydrated layers of this skin layer, thereby increasing the percutaneous absorption of a substance through this layer. Further, the device seeks a predetermined state of hydration, using this as a benchmark for standardizing permeability of a substance. Additionally, an advantage of the present method and device, is that as physiological changes occur at the site, for example, in the healing process, the treatment may be adjusted in response to the varying conditions. Thus, the site can be treated over long periods of time, thereby, for example, compensating for the healing process that replaces the stratum corneum, and normally limits further permeation of a substance. In this example, as the stratum corneum is replaced, the conductivity and hydration at the site falls, which would increasingly limit the permeation as the healing process continues. The current device may be used to detect this drop in conductivity and compensate by increasing the amount of substance released from the device.

The present method can be used for transport of a variety of systemically or locally acting pharmaceutical substances. For example, these substances may be nitroglycerin and anti-nauseants such as scopolamine, antibiotics such as tetracycline, streptomycin, sulfa drugs, kanamycin, neomycin, penicillin, or chloramphenicol. Various hormones such as LHRH, parathyroid hormone, growth hormone, gonadotropins, insulin, ACTH, somatostatin, prolactin, placental lactogen, melanocyte stimulating hormone, thyrotropin, parathyroid hormone, calcitonin, enkephalin, or angiotensin, steroidal or non-steroidal anti-inflammatory agents, and systemic antibiotic, antiviral or antifungal agents may also be transported.

As described below, the invention provides a number of therapeutic advantages and uses, however such advantages and uses are not limited by such description.

The Device

General Features

The device may be in a patch or may be combined with an energy delivery device for ablation or alteration of a membrane. An electrode may be placed in proximity to the target tissue site and a return electrode may be positioned distal from the first electrode so a current flow path is generated between the two electrodes when a power source is applied. The power source may be distal or integral to the unit. Either one or both electrodes may be placed within an electrically conducting liquid, such as isotonic saline. Optionally, the two electrodes may be used in conjunction with body fluids to create a galvanic cell whereby the current is generated by chemicals present in the body.

As current is applied between the electrodes, a sensor determines electrical properties in the created circuit, which may include, but not be limited to impedance, conductivity or resistance. Alternatively, chemical sensors may be applied at the target site for the detection of certain chemicals, such as lipids, proteins or salts. These may be detected by sensors located at the tip of a probe or an array of probes.

The information gathered regarding the electrical or chemical properties at the site is digitized and carried back to a remote processor within the device. The processor, in response to the nature of the information, then sends out a specific signal to a release mechanism juxtaposed to the target site. The release mechanism may be composed of an electronic or chemical valve, an electronically sensitive membrane, or a reactive membrane. The processed signal results in the release of a specified amount of the desired substance from a reservoir across the membrane and onto the target site. Additional, or continual, monitoring of the condition of the target site may optionally allow for the device to modulate the level of release over long periods of time in response to changes at the site.

In an alternative form of the device, the processed signal may result in an increase in the collection of fluids from the target site. The improved collection may be achieved, for example, by modulating an electronic or chemical valve, an electronically sensitive membrane, or a reactive membrane at the interface between the device and the target. One option includes the electrophoretic displacement of substances from the target site.

Use of the Device

Control Over Delivery of Pharmaceuticals

In general, the impedence of the skin can approach values as high as $10^8$ ohms×cm$^2$. As successive layers of the stratum corneum are removed, this impedance can drop to a fraction of that value. This drop in impedance can be monitored as a relative measure of the degree permeability to substances. An aspect of the invention is that, as an alternative to precise control over the depth of ablation, with the other parameters set, the depth of treatment can be precisely measured by assessing electrical or chemical properties at or across the target area (for example, impedence), and causing a feedback loop whereby the process controlling the release of the substance at the target site is modulated according to the measured parameters. Therefore, various settings on the device can be adjusted to allow incremental increases or decreases to the amount of substance released.

Alternatively, a probe placed adjacent the ablation site on tissue in combination with an electrically conducting dissimilar metal plate in contact with tissue at a location remote from the ablation site and an electrolyte defined by the intervening tissue create a galvanic cell when the tip and plate have different work functions because of migration of electrical charges therebetween. The current that flows between the electrodes is related to the exposure to electrochemicals which may leech from the target area as increasing hydration is encountered.

Control of Toxicity of Pharmaceuticals

One of the limitations of transcutaneous delivery of drug formulations is that the drug can be locally toxic at high doses, and therefore must be modulated to permeate the skin at a controlled rate. In the present case, modulation may occur by limiting the dosage at the treatment site. Depth of treatment and levels of hydration can be correlated with the change in impedance across the site as the stratum corneum is reduced. When a particular depth or hydration level is reached, a relative permeability associated with that level of hydration may be designated.

The present invention provides a means for treating local pain or infections, or for application of a substance to a small specified area, directly, thus eliminating the need to provide high, potentially toxic amounts systemically through oral or intravenous administration. Locally acting pharmaceuticals such as alprostadil (for example, Caverject from Pharmacia & Upjohn), various antibiotics, antiviral or antifungal agents, or chemotherapy or anti-cancer agents, can be delivered using this method to treat regions proximal to the delivery site. Protein or DNA based biopharmaceutical agents can also be delivered using this method.

Delivery of Immunogens

Antigens derived from a virus, bacteria or other agent which stimulates an immune response can be administered through the skin for immunization purposes. The antigen is delivered through the outer layers of the stratum corneum, either singly or multiply, and the immunogen is provided in an appropriate formulation. For booster immunizations, where delivery over a period of time increases the immune response, the immunogen can be provided in a formulation that penetrates slowly through the treatment site, but at a rate faster than possible through unaltered skin.

Delivery of Anti-Inflammatory Drugs

Analgesics and other non-steroidal anti-inflammatory agents, as well as steroidal anti-inflammatory agents, may be caused t o permeate through reduced stratum corneum to locally affect tissue within proximity of the irradiated site. For example, anti-inflammatory agents such as Indocin (Merck & Co.), a non-steroidal drug, are effective agents for treatment of rheumatoid arthritis when taken orally, yet sometimes debilitating gastrointestinal effects can occur. By administering such agents through laser-assisted perforation or alteration sites, these potentially dangerous gastrointestinal complications may be avoided. Further, high local concentrations of the agents may be achieved more readily near the site of irradiation as opposed to the systemic concentrations achieved when orally administered.

The alteration of the stratum corneum causes a local increase in the water loss through the skin (referred to as transepidermal water loss, or TEWL). With successive reduction of the stratum corneum, there is a corresponding increase in water loss. The presence of water at the target site may alternatively be used, for example, as a means to solubilize the release membrane on the device, thereby allowing for release of the desired substance.

Alteration without Ablation

The present device allows for control of delivery where variable amounts of stratum corneum are removed from skin. The technique of successive removal of layers of dead or necrotic cells of the stratum corneum provides several advantages. Preferably, the stratum corneum is reduced, but not removed, so that its structural and biochemical makeup still permit drugs to permeate. Therefore, the skin after irradiation still presents a barrier, albeit reduced, to external factors such as viruses and chemical toxins. Less energy is required for reduction than is required to entirely remove the stratum corneum, thus smaller and cheaper devices can be used. The technique also minimizes the damage to surrounding tissues providing a more rapid and efficient replacement of the stratum corneum.

Eventually, there is an even lesser threshold energy reached where ablation does not occur, but reduction of the skin's barrier function takes place, perhaps through molecular alterations of the biomolecules that make up the stratum corneum. In this case enhanced permeation of topically applied compounds or enhanced removal of biomolecules such as insulin from the body can also take place.

Embodiments of the present invention are better illustrated with reference to the Figure(s), however, such reference is not meant to limit the present invention in any fashion. The embodiments and variations described in detail herein are to be interpreted by the appended claims and equivalents thereof.

One embodiment of a membrane drug delivery device is illustrated by FIG. 1. The patch 1 basically includes a first electrode 2, which may act as an anode, and a second electrode 3, which may act as a cathode. The patch 1 is placed against the skin 4 of a patient so that the anode electrode 2 and cathode electrode 3 are in electrical communication with the patient's skin 4. Adjacent to the anode 2 is a container 5 or other suitable structure defining a well for holding a substance or medication 6 in place between the anode 2 and the skin 4 of the patient. When a voltage Va is impressed across the first and second electrodes 2,3, a current Ia will flow through the skin 4 of the patient and be detected by a controller 7 which monitors between the first and second electrodes 2,3. A microprocessor (not shown) within the controller 7 circuit is designed to interpret changes in electrical properties of the target site on the skin 4 and provide an adjustable signal Ib to a release mechanism 8 located between a reservoir 5 and an optional permeable membrane 9 which is in contact with the skin 4 or in contact with a fluid (not shown) at the patch-skin interface.

The controller 7 circuit is designed to send a metered signal to the release mechanism 8 such that a controlled amount of the substance 6 becomes available to the permeable membrane 9. The controller 7 additionally responds to changes in the condition of the target site on the skin 4. For example, an increase in impedence during replacement of stratum corneum would signal that more of the substance 6 may be released from the patch in order to compensate for changes in permeability at the target site on the skin 4 arising from the change in the impedence.

Figure 2:
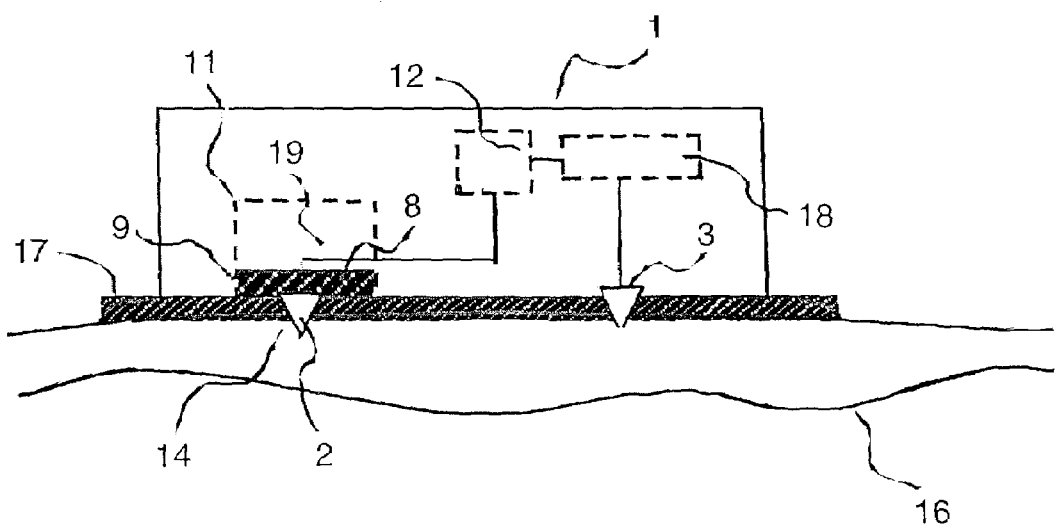
FIG. 2 shows a schematic-of a device used to alter or ablate a membrane and deliver a controlled amount of substance to a site.

With continued reference to FIG. 1 FIG. 2 depicts another embodiment of the device. The device contains a patch 1 with an energy delivery system 12 integrated therein. The patch 1 further comprises a reservoir 11, a release mechanism 8 located between the reservoir 11 and an optional permeable membrane 9 which is in contact with the target site 14 or in contact with a fluid 17 at the patch-skin interface. The energy delivery system 12 is capable of delivering energy to a target site 14 on a biological membrane 16 resulting in an ablation or alteration of the membrane 16 at the site 14. At least one electrode 2 is in electrical contact with the ablation site 14.

This contact may optionally involve an electrically conductive fluid interface 17 that improves the flow of charges between the electrode surface 2 and the treatment site 14. A second electrode 3 may be located distally from the first electrode 2 such that the membrane forms a bridge between the electrodes 2,3. The electrodes 2,3 may be composed of similar or different materials. A microprocessor (not shown) present in a controller 18 generates a current across the electrodes 2,3. Alternatively, the two electrodes 2,3 form part of a galvanic cell that distributes a current based on the migration of ions between them.

The controller 18 detects changes in the current and, according to an algorithm, sends a signal to a release mechanism 8 at the interface between a reservoir 11 containing a substance 19 and the site 14. Optionally, the interface may contain a membrane 9 or liquid 17. In one embodiment the signal generated by the controller 18 causes the release of a substance 19, e.g. a medicament, from-the reservoir 11. Alternatively, the signal may result in the generation of a directional current between the reservoir 11 and the site 14, such that ions of the medicament 19 are caused to flow to or from the target site 14.

Any patents or publications mentioned in this specification are indicative of the levels of those skilled in the art to which the invention pertains. These patents and publications are herein incorporated by reference to the same extent as if each individual publication was indicated to be incorporated specifically and individually by reference.

One skilled in the art will readily appreciate that the present invention is well adapted to carry out the objects and obtain the ends and advantages mentioned, as well as those inherent therein. It will be apparent to those skilled in the art that various modifications and variations can be made in practicing the present invention without departing from the spirit or scope of the invention. Changes therein and other uses will occur to those skilled in the art which are encompassed within the spirit of the invention as defined by the scope of the claims.

What is claimed is:

1. A device for controlling the release of a substance at a site of interest in a biological membrane comprising:
    a feedback means for determining relative permeability of the membrane at said site of interest; and
    a means of releasing a variable amount of said substance to the site of interest; said amount varying in response to the status of a monitored physiological state.

2. The device of claim 1, wherein said feedback means comprises:
    at least one first active electrode comprising an anode in electrical contact at the site of interest;
    a second return electrode comprising a cathode in electrical contact distal to said first electrode at the site of interest; and
    a controller to monitor an electrical current between said first electrode and said second electrode, said controller further comprising a microprocessor.

3. The device of claim 1, wherein said feedback means comprises:
    at least one probe further comprising an electrical sensor, a chemical sensor or a mechanical sensor, said sensor located at the tip of said probe(s) and said sensor in contact with the site of interest; and
    a controller to monitor said probe(s), said controller further comprising a microprocessor.

4. The device of claim 1, wherein said means of releasing the variable amount of said substance comprises:
    a reservoir to contain said substance; and
    a release mechanism located between said reservoir and the site of interest; said mechanism operably connected to a controller; wherein operation of said mechanism by said controller releases said substance from said reservoir to the site of interest or collects said substance in said reservoir from the site of interest.

5. The device of claim 4, further comprising a permeable membrane located between said release mechanism and said site of interest, wherein said permeable membrane is in contact with said site of interest or in contact with a fluid at said site of interest.

6. The device of claim 4, wherein said release mechanism is a valve, a membrane or an electronic pump device.

7. The device of claim 6, wherein said electronic pump device is an electrophoretic device.

8. The device of claim 1, wherein said device is in a patch.

9. The device of claim 1, wherein the biological membrane is the skin.

10. The device of claim 9, wherein the skin has an ablated or altered stratum corneum at the site of interest.

11. The device of claim 1, wherein said physiological state comprises an electrical property or a chemical property of the site of interest.

12. The device of claim 11, wherein said electrical property is impedance or conductivity.

13. The device of claim 1, wherein said chemical property is hydration or one or more ion levels at the site of interest.

14. The device of claim 13, wherein said chemical property is the level of lipids, proteins or carbohydrates at the site of interest.

15. The device of claim 1, wherein said substance is a pharmaceutical compound.

16. The device of claim 15, wherein said pharmaceutical compound is selected from the group consisting of nitroglycerin, an anti-nauseant, an antibiotic, a hormone, a steroidal antinflammatory agent, a non-steroid anti-inflammatory agent, a chemotherapeutic agent, an anti-cancer agent, an immunogen, an anti-viral agent or an anti-fungal agent.

17. The device of claim 16, wherein said anti-nauseant is scopolamine.

18. The device of claim 16, wherein said antibiotic is tetracycline, streptomycin, sulfa drugs, kanamycin, neomycin, penicillin, or chloramphenicol.

19. The device of claim 16, wherein said LHRH, hormone is parathyroid hormone, growth hormone, gonadotropins, insulin, ACTH, somatostatin, prolactin, placental lactogen, melanocyte stimulating hormone, thyrotropin, parathyroid hormone, calcitonin, enkephalin, or angiotensin.

20. The device of claim 1, wherein said substance is a diagnostic material.

21. A method to control the release of a substance at a site of interest in a biological membrane comprising the steps of:
   contacting the site of interest with the device of claim 1;
   monitoring a physiological state at the site of interest;
   applying an algorithm to evaluate said physiological state;
   operating a release mechanism in the device of claim 1 in response to said value obtained for said physiological state; and
   releasing said substance to the site of interest or collecting said substance from the site of interest thereby controlling the release of said substance at the site of interest.

22. The method of claim 21, wherein said value obtained for said physiological state is compared to a control value of said physiological state.

23. The method of claim 22, wherein said control value of said physiological state is obtained from the same individual or within a group of individuals.

* * * * *